(12) United States Patent
Goto et al.

(10) Patent No.: US 11,458,237 B2
(45) Date of Patent: Oct. 4, 2022

(54) BLOOD PURIFICATION APPARATUS

(71) Applicant: Nikkiso Company Limited, Tokyo (JP)

(72) Inventors: Hitoshi Goto, Shizuoka (JP); Kunihiko Akita, Shizuoka (JP); Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 432 days.

(21) Appl. No.: 16/596,936

(22) Filed: Oct. 9, 2019

(65) Prior Publication Data
US 2020/0038577 A1    Feb. 6, 2020

Related U.S. Application Data

(63) Continuation of application No. PCT/JP2018/014954, filed on Apr. 9, 2018.

(30) Foreign Application Priority Data

Apr. 10, 2017 (JP) .............................. JP2017-077399

(51) Int. Cl.
*A61M 1/36* (2006.01)
*A61B 5/024* (2006.01)

(52) U.S. Cl.
CPC .......... *A61M 1/3656* (2014.02); *A61B 5/024* (2013.01); *A61M 1/3669* (2013.01); *A61M 2205/13* (2013.01)

(58) Field of Classification Search
CPC .... A61M 1/3656; A61M 1/3669; A61B 5/024
See application file for complete search history.

(56) References Cited

U.S. PATENT DOCUMENTS

| | | | | |
|---|---|---|---|---|
| 2004/0254513 A1* | 12/2004 | Shang | ................. | A61M 1/1601 210/746 |
| 2008/0195021 A1* | 8/2008 | Roger | ................. | A61M 1/3639 604/4.01 |
| 2017/0361004 A1* | 12/2017 | Toyoda | ............... | A61M 1/3656 |

FOREIGN PATENT DOCUMENTS

| | | | |
|---|---|---|---|
| EP | 2117625 B1 | 11/2012 | |
| JP | 2005-065888 A | 3/2005 | |
| | (Continued) | | |

OTHER PUBLICATIONS

International Search Report for Application No. PCT/JP2018/014594, dated Jun. 26, 2018, pp. 1-4.

(Continued)

*Primary Examiner* — Ariana Zimbouski
*Assistant Examiner* — Roy Kim
(74) *Attorney, Agent, or Firm* — Young Basile Hanlon & MacFarlane, P.C.

(57) ABSTRACT

A blood purification apparatus that detects dislodgement of a puncture needle is provided. The apparatus includes an arterial electrode, a venous electrode, a power source capable of causing a current to flow through an arterial puncture needle and a venous puncture needle that are stuck in a patient, a body-surface electrode closely attached to a body surface of the patient, a detection device capable of acquiring a heart rate of the patient in accordance with an electrical signal detected by the body-surface electrode, a monitoring device capable of monitoring in real time the current flowing through the arterial electrode or the venous electrode and a change in an impedance in a body of the patient that is detected by the detection device, and an identifying device capable of identifying a dislodged state where the arterial puncture needle or the venous puncture needle is dislodged from the patient, in accordance with the (Continued)

change in the impedance that is an object of monitoring by the monitoring device.

9 Claims, 5 Drawing Sheets

(56) References Cited

FOREIGN PATENT DOCUMENTS

| | | | |
|---|---|---|---|
| JP | 2006-110120 A | 4/2006 | |
| JP | 4568706 B2 * | 10/2010 | .......... A61M 1/3656 |
| JP | 2013-081817 A | 5/2013 | |
| JP | 2014-208312 A | 11/2014 | |
| KR | 20110005875 A * | 1/2011 | .............. A61M 1/36 |

OTHER PUBLICATIONS

European Search Report for Application No. 18784043.4, dated Dec. 9, 2020.

* cited by examiner

[Fig. 1]
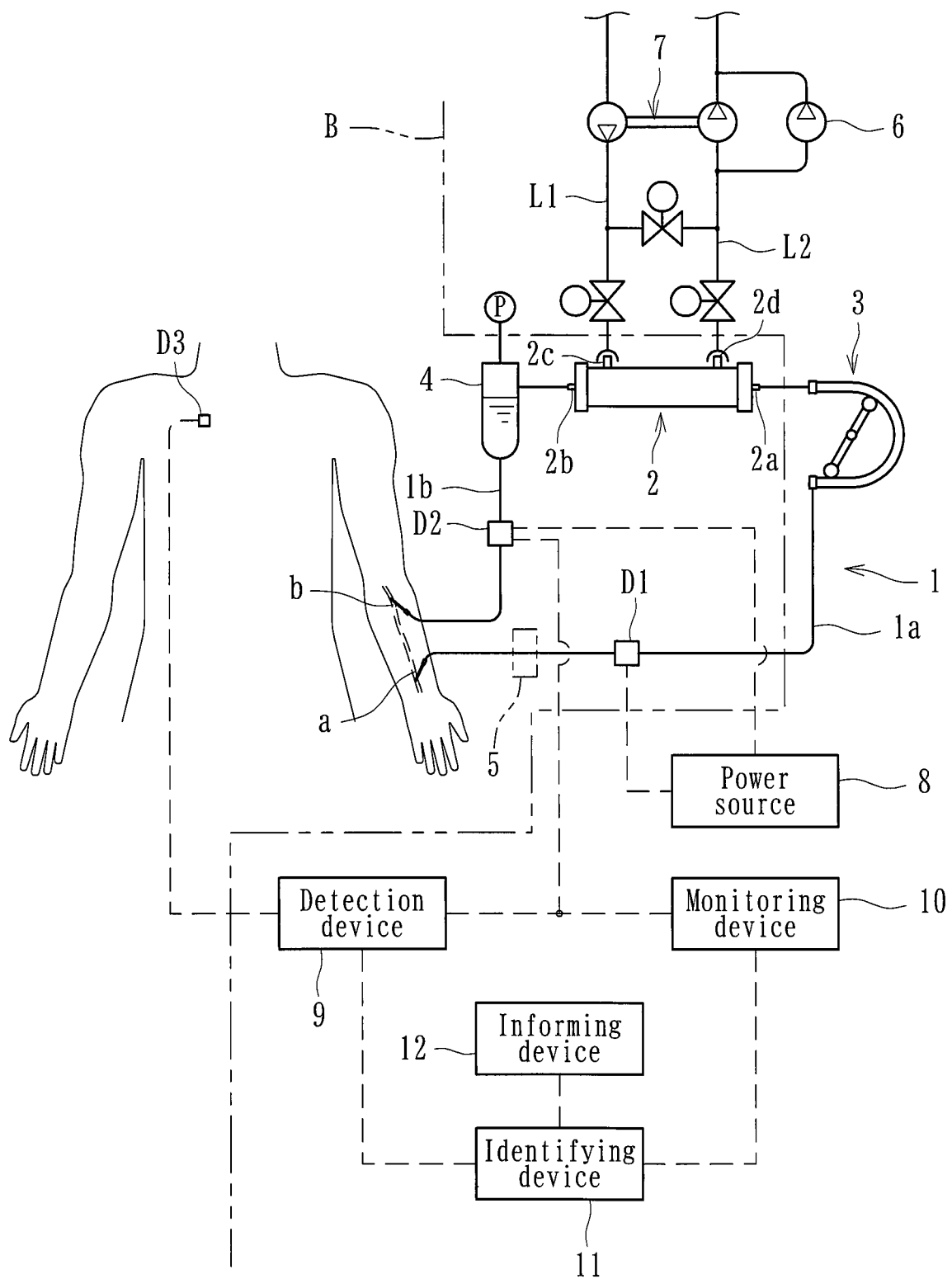

[Fig. 2]
(a)
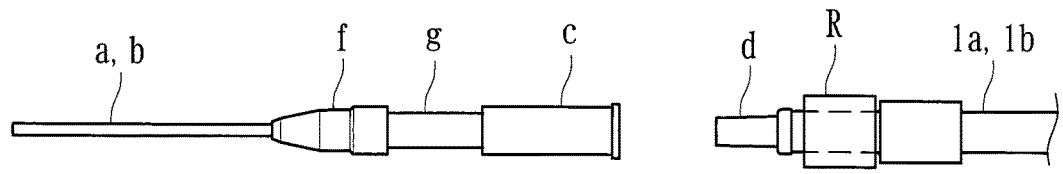
(b)
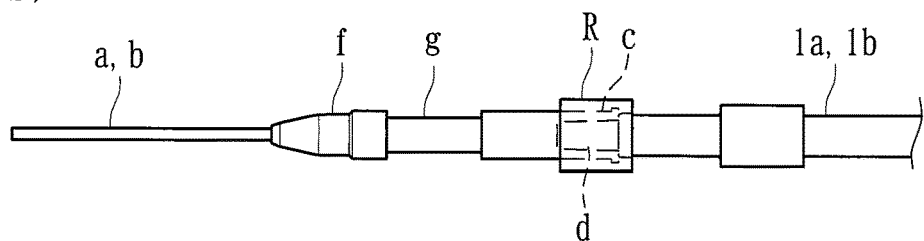
[Fig. 3]
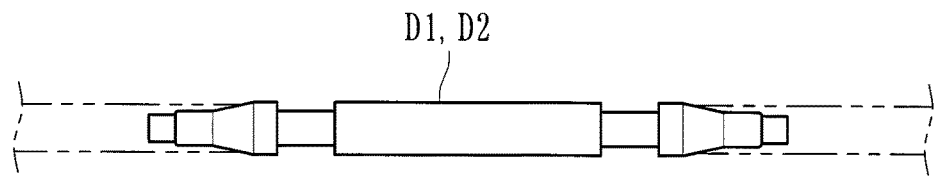
[Fig. 4]
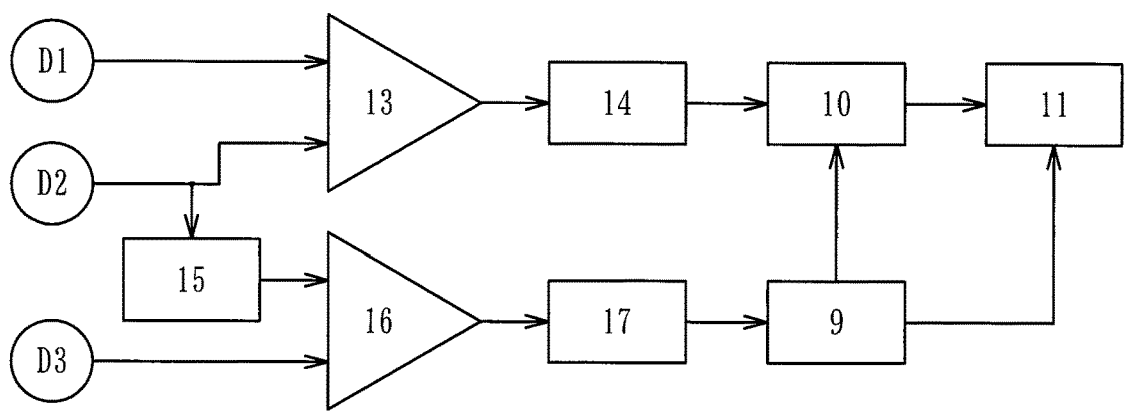
D1: Arterial
D2: Venous
D3: Body surface
13, 16: Differential amplifier
14: Rectifier circuit
15: Impedance-adjusting device
17: High frequency Cut-Off filter
9: Detection device
10: Monitoring device
11: Identifying device

[ Fig. 5 ]
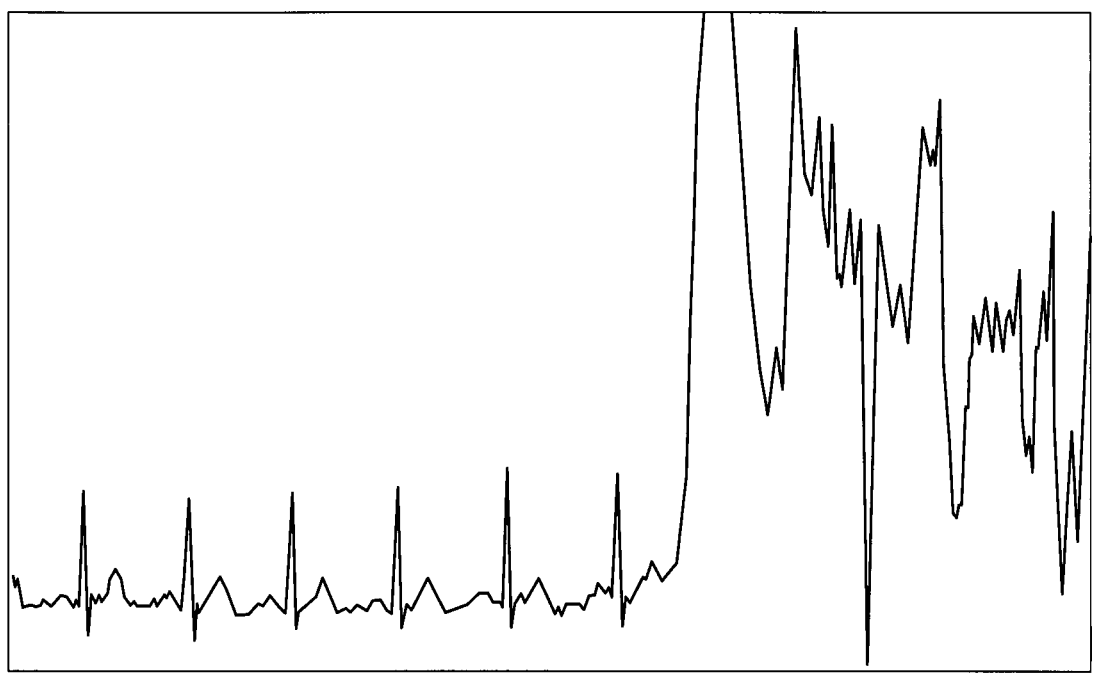
[ Fig. 6 ]
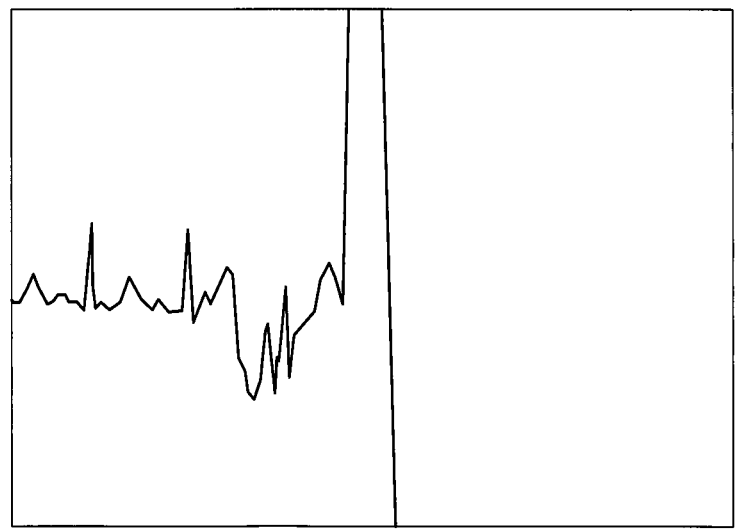

[ Fig. 7 ]

(a) Body-surface electrode D3 is in Unstable contact/detached

|  | Unstable contact | Detached |
|---|---|---|
| Identification of needle dislodgement | Normal | Normal |
| Heart-rate detection | Much noise | Undetectable |

(b) Arterial electrode D1 is in Unstable contact/detached

|  | Unstable contact | Detached |
|---|---|---|
| Identification of needle dislodgement | Much noise | Misidentified |
| Heart-rate detection | Normal | Normal |

(c) Venous electrode D2 is in Unstable contact/detached

|  | Unstable contact | Detached |
|---|---|---|
| Identification of needle dislodgement | Much noise | Misidentified |
| Heart-rate detection | Much noise | Undetectable |

[Fig. 8]

(a) Puncture with Arterial puncture needle a is unstable / Arterial puncture needle a is dislodged

|  | Unstable puncture | Dislodged |
|---|---|---|
| Identification of needle dislodgement | Much noise | Identified |
| Heart-rate detection | Normal | Normal |

(b) Puncture with Venous puncture needle b is unstable / Venous puncture needle b is dislodged

|  | Unstable puncture | Dislodged |
|---|---|---|
| Identification of needle dislodgement | Much noise | Identified |
| Heart-rate detection | Much noise | Undetectable |

BLOOD PURIFICATION APPARATUS

FIELD

The present invention relates to a blood purification apparatus capable of purifying blood of a patient that is caused to extracorporeally circulate through an arterial blood circuit and a venous blood circuit.

BACKGROUND

In general, dialysis treatment is performed with a dialysis treatment apparatus including a blood circuit for extracorporeal circulation of blood of a patient, a dialyzer connected to a halfway position of the blood circuit, a peristaltic blood pump, and a dialysis device capable of performing ultrafiltration while performing hemodialysis treatment by introducing and delivering dialysate into and from the dialyzer. Typically, dialysis treatment performed with such a dialysis treatment apparatus is conducted for about four hours every other day. Therefore, the hemodynamics of the patient changes greatly during the treatment. In particular, it is an important issue to effectively and assuredly prevent the reduction in blood pressure due to removal of excessive water (ultrafiltration).

Furthermore, many of patients who need to take dialysis treatment have a cardiovascular complication such as arrhythmia. Therefore, any hemodynamic abnormality and the cause for such abnormality need to be grasped by monitoring heart rate, pulse, and so forth. As a device for monitoring information on the heart rate or the pulse of the patient, an electrocardiograph capable of measuring an electrocardiogram is generally used. For example, during blood purification treatment, at least a pair of electrodes (an electrocardiographic measurement device) are closely attached to the patient, and an electrocardiogram of the patient is measured from the potentials of the electrodes.

On the other hand, in blood purification treatment, an arterial puncture needle and a venous puncture needle are stuck into the patient, and blood of the patient is collected from the arterial puncture needle and is purified while being caused to extracorporeally circulate through the blood circuit. The purified blood needs to be returned to the patient from the venous puncture needle. While the blood is in extracorporeal circulation, the puncture needles may be accidentally dislodged from the puncture site of the patient because of a body movement or the like, for example. In particular, if the venous puncture needle is dislodged, the blood may leak to the outside. To detect such dislodgement of the puncture needle, there is a proposal of a blood purification apparatus capable of identifying a dislodged state of a puncture needle while measuring an electrocardiogram (see PTL 1, for example).

PTL 1: Japanese Unexamined Patent Application Publication No. 2014-208312, which is incorporated by reference herein for all purposes

SUMMARY

In the above known technique, however, if an electrocardiogram electrode (a body-surface electrode) closely attached to the body surface is detached, the dislodged state of the puncture needle cannot be identified. Therefore, from the viewpoint of safety, the blood purification treatment may be suspended inevitably. Specifically, if the body-surface electrode is detached from the patient, the blood purification treatment does not need to be immediately suspended but the dislodged state of the puncture needle cannot be identified. Therefore, as a matter of safety, the blood purification treatment needs to be suspended for safety confirmation.

The present teachings have been conceived in view of the above circumstances and provides a blood purification apparatus capable of continuously performing the identification of a dislodged state of an arterial puncture needle or a venous puncture needle even if a body-surface electrode is detached from the patient.

According to the teachings herein, there is provided a blood purification apparatus including an arterial blood circuit provided with an arterial puncture needle at a distal end, the arterial puncture needle being stickable into a patient; a venous blood circuit provided with a venous puncture needle at a distal end, the venous puncture needle being stickable into the patient; and a blood purification device connected to a proximal end of the arterial blood circuit and to a proximal end of the venous blood circuit, the device purifying blood of the patient that extracorporeally circulates through the arterial blood circuit and the venous blood circuit. The blood purification apparatus includes an arterial electrode through which a voltage is applied to the blood flowing in the arterial blood circuit; a venous electrode through which the voltage is applied to the blood flowing in the venous blood circuit; a power source that causes a current to flow in the blood through the arterial puncture needle and the venous puncture needle that are stuck in the patient, by applying the voltage between the arterial electrode and the venous electrode; a body-surface electrode closely attached to a body surface of the patient and that detects an electrical signal from a body of the patient; a detection device that acquires a predetermined vital parameter by detecting a change in an impedance in the body of the patient in accordance with the electrical signal detected by the body-surface electrode; a monitoring device that monitors in real time the current flowing through the arterial electrode or the venous electrode, and the change in the impedance in the body of the patient that is detected by the detection device; and an identifying device that identifies a dislodged state where the arterial puncture needle or the venous puncture needle is dislodged from the patient, in accordance with the change in the impedance that is an object of monitoring by the monitoring device.

According to the teachings herein, in the blood purification apparatus taught herein, when the identifying device identifies any dislodged state, the identifying device identifies which of the arterial puncture needle and the venous puncture needle is dislodged.

According to the teachings herein, in the blood purification apparatus taught herein, the arterial electrode or the venous electrode also serves as a counter electrode for the detection device to detect the change in the impedance.

According to the teachings herein, in the blood purification apparatus taught herein, the arterial blood circuit is provided with a bubble detection device at a distal end part, the bubble detection device detecting a flow of bubbles, and wherein the identifying device identifies the dislodgement of the arterial puncture needle with the detection of bubbles by the bubble detection device.

According to the teachings herein, in the blood purification apparatus taught herein, the identifying device that identifies the dislodged state of the arterial puncture needle or the venous puncture needle further identifies whether a state of puncture is unstable or whether any of the electrodes is in unstable contact or is detached.

According to the teachings herein, the blood purification apparatus taught herein further includes an informing device that provides information on the dislodged state if the identifying device identifies the arterial puncture needle or the venous puncture needle to be in the dislodged state.

According to the teachings herein, the power source is capable of causing a current to flow through the arterial puncture needle and the venous puncture needle that are stuck in the patient, by applying a voltage between the arterial electrode and the venous electrode. Therefore, even if the body-surface electrode is detached from the patient, the identification of a dislodged state of the arterial puncture needle or the venous puncture needle can be performed continuously.

According to the teachings herein, when the identifying device identifies any dislodged state, the identifying device identifies which of the arterial puncture needle and the venous puncture needle is dislodged. Therefore, a countermeasure for the dislodgement can be taken accurately and smoothly.

According to the teachings herein, the arterial electrode or the venous electrode also serves as a counter electrode for the detection device to detect the change in the impedance. Therefore, the number of electrodes to be attached in the blood purification treatment can be reduced, and the ease of work can be increased.

According to the teachings herein, the bubble detection device that detects the flow of bubbles is attached to the distal end part of the arterial blood circuit, and the identifying device identifies the dislodgement of the arterial puncture needle with the detection of bubbles by the bubble detection device. Therefore, when any dislodged state is identified, the dislodged state can be distinguished more accurately between the dislodged state of the arterial puncture needle and the dislodged state of the venous puncture needle.

According to the teachings herein, in addition to the dislodged state of the arterial puncture needle or the venous puncture needle, the identifying device identifies whether the state of puncture is unstable or whether the electrode is in unstable contact or is detached. Therefore, a countermeasure can be taken before any dislodged state occurs or before any of the electrodes (the arterial electrode, the venous electrode, or the body-surface electrode) is detached.

According to the teachings herein, if the identifying device identifies the arterial puncture needle or the venous puncture needle to be in the dislodged state, the informing device provides information on the dislodged state. Therefore, medical staff or the like nearby can immediately notice the dislodged state and can immediately take a countermeasure.

BRIEF DESCRIPTION

FIG. 1 is an overall diagram illustrating a blood purification apparatus according to an embodiment of the present invention.

FIG. 2 includes diagrams illustrating a puncture needle (an arterial puncture needle or a venous puncture needle) included in the blood purification apparatus.

FIG. 3 is a diagram illustrating an electrode (an arterial electrode or a venous electrode) included in the blood purification apparatus.

FIG. 4 is a block diagram illustrating a system configuration of the blood purification apparatus.

FIG. 5 is a graph illustrating a value (with much noise) detected by a detection device included in the blood purification apparatus.

FIG. 6 is a graph illustrating a value (that intermits) detected by the detection device included in the blood purification apparatus.

FIG. 7 includes tables each summarizing statuses of identification of needle dislodgement and statuses of detection of heart rate in a case where a corresponding one of a body-surface electrode, the arterial electrode, and the venous electrode included in the blood purification apparatus is in unstable contact and in a case where the electrode is detached.

FIG. 8 includes tables each summarizing statuses of identification of needle dislodgement and statuses of detection of heart rate in a case where puncture with a corresponding one of the venous puncture needle and the arterial puncture needle included in the blood purification apparatus is unstable and in a case where the needle is dislodged.

DETAILED DESCRIPTION

An embodiment of the present teachings will now be described specifically with reference to the drawings.

A blood purification apparatus according to the present embodiment is a hemodialysis apparatus intended for hemodialysis treatment and ultrafiltration that are performed while blood of a patient is caused to extracorporeally circulate. As illustrated in FIG. 1, the blood purification apparatus includes a blood circuit 1, a dialyzer 2 as a blood purification device connected to the blood circuit 1, a dialysate introduction line L1 and a dialysate drain line L2 provided in an apparatus body B, an arterial electrode D1, a venous electrode D2, a body-surface electrode D3, a power source 8, a detection device 9, a monitoring device 10, an identifying device 11, and an informing device 12.

The blood circuit 1 is formed of a flexible tube through which fluid such as blood is allowed to flow. The blood circuit 1 includes an arterial blood circuit 1a and a venous blood circuit 1b. The arterial (blood-removal or blood-collection) blood circuit 1a is provided with an arterial puncture needle (a) (see FIGS. 1 and 2) connectable to a distal end thereof, and with a peristaltic blood pump 3 at a halfway position thereof. The venous (blood-returning) blood circuit 1b is provided with a venous puncture needle (b) (see FIGS. 1 and 2) connected to a distal end thereof, and with an air-trap chamber 4 for bubble removal at a halfway position thereof. In this specification, the side of the puncture needle provided for blood removal (blood collection) is referred to as the "arterial" side, and the side of the puncture needle provided for blood returning is referred to as the "venous" side. The "arterial" side and the "venous" side are not defined in accordance with which of the artery and the vein is to be the object of puncture.

The arterial puncture needle (a) and the venous puncture needle (b) according to the present embodiment are each a puncture needle (an accessing device) that is stickable into a patient. As illustrated in FIG. 2, the arterial puncture needle (a) and the venous puncture needle (b) are each a cannula (an intravascular indwelling needle) attached to a distal end part (f) made of rigid resin or the like. The distal end part (f) is connected to a joint (c), which is made of rigid resin or the like, through a clamping flexible tube (g). As illustrated in part (a) of the drawing, the distal end part (f), the clamping flexible tube (g), and the joint (c) are integrated into a unit.

The distal end of the arterial blood circuit 1a and the distal end of the venous blood circuit 1b each have a joint d made of rigid resin or the like. As illustrated in part (b) of the drawing, the joint (c) on the puncture-needle side is fitted onto the joint (d) and is screwed thereto with a lock ring R, whereby the fitted state can be locked. If the clamping flexible tube (g) is clamped with a pair of forceps, the flow route between the arterial puncture needle (a) or the venous puncture needle (b) and the arterial blood circuit 1a or the venous blood circuit 1b can be closed.

When the peristaltic blood pump 3 is activated with the arterial puncture needle (a) and the venous puncture needle (b) being stuck in the patient, blood of the patient that is collected from the arterial puncture needle (a) flows through the arterial blood circuit 1a and reaches the dialyzer 2, where the blood is purified. Then, the blood flows through the venous blood circuit 1b while bubbles generated therein are removed in the air-trap chamber 4, and returns into the body of the patient through the venous puncture needle (b). Thus, the blood of the patient can be purified by the dialyzer 2 while being caused to extracorporeally circulate through the blood circuit 1.

The dialyzer 2 has, in a housing thereof, a blood introduction port 2a, a blood delivery port 2b, a dialysate introduction port 2c, and a dialysate delivery port 2d. The blood introduction port 2a receives a proximal end of the arterial blood circuit 1a that is connected thereto. The blood delivery port 2b receives a proximal end of the venous blood circuit 1b that is connected thereto. The dialysate introduction port 2c and the dialysate delivery port 2d are connected to the dialysate introduction line L1 and the dialysate drain line L2, respectively, extending from the apparatus body B.

The housing of the dialyzer 2 houses a plurality of hollow fibers. The inside of each of the hollow fibers serves as a blood flow route. The space between the outer peripheral surface of each of the hollow fibers and the inner peripheral surface of the housing serves as a dialysate flow route. The hollow fibers each have a number of very small holes (pores) extending therethrough from the outer peripheral surface to the inner peripheral surface, thereby forming a hollow fiber membrane. Impurities and the like contained in the blood are allowed to penetrate through the membranes into the dialysate.

As illustrated in FIG. 1, the apparatus body B includes a duplex pump 7 provided over the dialysate introduction line L1 and the dialysate drain line L2, and an ultrafiltration pump 6 connected to a bypass line connected to the dialysate drain line L2 in such a manner as to bypass the duplex pump 7. One end of the dialysate introduction line L1 is connected to the dialyzer 2 (the dialysate introduction port 2c), and the other end is connected to a dialysate supply device (not illustrated) that prepares a dialysate at a predetermined concentration. One end of the dialysate drain line L2 is connected to the dialyzer 2 (the dialysate delivery port 2d), and the other end is connected to a drainage device (not illustrated). The dialysate supplied from the dialysate supply device flows through the dialysate introduction line L1 into the dialyzer 2, and then flows through the dialysate drain line L2 into the drainage device.

The ultrafiltration pump 6 is provided for removing water from the blood of the patient that flows through the dialyzer 2. That is, when the ultrafiltration pump 6 is activated, the amount of liquid drained through the dialysate drain line L2 becomes greater than the amount of dialysate introduced through the dialysate introduction line L1. Hence, water is removed from the blood by an amount corresponding to the excess. Water may be removed from the blood of the patient with another device (such as a device employing a so-called balancing chamber or the like) instead of the duplex pump 7.

A bubble detection device 5 is a sensor capable of detecting bubbles (air) flowing in the flexible tube forming the arterial blood circuit 1a. The bubble detection device 5 includes, for example, an ultrasonic vibrator formed of a piezoelectric device, and an ultrasonic receiver formed of a piezoelectric device. The bubble detection device 5 is capable of emitting ultrasonic waves from the ultrasonic vibrator toward the flexible tube forming the arterial blood circuit 1a, and is also capable of receiving the thus generated vibration by the ultrasonic receiver.

The ultrasonic receiver is configured to generate a voltage that changes with the vibration received. The ultrasonic receiver is capable of detecting the flow of bubbles by the fact that the detected voltage has exceeded a predetermined threshold. Specifically, the ultrasonic attenuation factor of bubbles is higher than those of blood and substitution solutions. Hence, the ultrasonic waves transmitted through the liquid are detected. Then, if the detected voltage has exceeded the predetermined threshold, it is regarded that the flow of bubbles (gas) has been detected.

In the present embodiment, the arterial electrode D1, the venous electrode D2, and the body-surface electrode D3 are provided. The arterial electrode D1 is an electrode attached to the arterial blood circuit 1a (between a position where the peristaltic blood pump 3 is provided and the arterial puncture needle (a) and through which a voltage can be applied to the blood flowing in the arterial blood circuit 1a. The venous electrode D2 is an electrode attached to the venous blood circuit 1b (between a position where the air-trap chamber 4 is provided and the venous puncture needle (b) and through which a voltage can be applied to the blood flowing in the venous blood circuit 1b.

As illustrated in FIG. 3, the arterial electrode D1 and the venous electrode D2 are conductive members connected to the respective flexible tubes and are each electrically connected to the power source 8 with a connecting device such as an alligator clip. Hence, a predetermined voltage can be applied to the blood flowing thereinside. The arterial electrode D1 and the venous electrode D2 are each not limited to the one illustrated in FIG. 3 and may each be a device of any other type (including a device not being directly in contact with blood), as long as the voltage of the power source 8 can be applied to the blood flowing in the arterial blood circuit 1a or the blood flowing in the venous blood circuit 1b.

The power source 8 is capable of applying a voltage that generates a weak current (1 mA or lower) at a high frequency (several kHz to several tens of kHz) between the arterial electrode D1 and the venous electrode D2. With such a voltage application, a current flows through the arterial puncture needle (a) and the venous puncture needle (b) that are stuck in the patient. Specifically, the blood that extracorporeally circulates through the arterial blood circuit 1a and the venous blood circuit 1b is a conductor that allows a current to flow therethrough. Hence, as long as the puncture with the arterial puncture needle (a) and the venous puncture needle (b) is normal, a current flows through the arterial puncture needle (a) and the venous puncture needle (b) at the application of a voltage from the power source 8.

The body-surface electrode D3 is closely attached to the body surface (skin) of the patient and is capable of detecting an electrical signal from the body of the patient. In the present embodiment, the body-surface electrode D3 is capable of measuring an electrocardiogram (vital information) of the patient. The body-surface electrode D3 is an electrode closely attached to a position across the heart from the puncture sites for the arterial puncture needle (a) and the venous puncture needle (b). The body-surface electrode D3 is electrically connected to the detection device 9.

In the present embodiment, as illustrated in FIG. 4, the arterial electrode D1 and the venous electrode D2 are connected to a differential amplifier 13, the venous electrode D2 is also connected to an impedance-adjusting device 15, and the body-surface electrode D3 and the impedance-adjusting device 15 are connected to a differential amplifier 16. Thus, impedances for the measured voltage to be inputted to the differential amplifier 13 and for the measured voltage to be inputted to the differential amplifier 16 are adjusted.

That is, there is a difference between "the impedance of body fluid and the impedance of skin" acquired through the body-surface electrode D3 and the venous electrode D2 and "the impedance of blood" acquired through the arterial electrode D1 and the venous electrode D2, and the difference is adjustable by the impedance-adjusting device 15. The impedance-adjusting device 15 is preferably a device that adjusts the applied resistance with a variable resistor or the like, a device that employs an adjustment technique of automatic gain control (AGC) so that a heart-rate component can be extracted, or the like.

The differential amplifier 13 is connected to the monitoring device 10 through a rectifier circuit 14. The differential amplifier 16 is connected to the detection device 9 through a high frequency cut-off filter 17. Therefore, an electrical signal generated by the differential amplifier 16 is inputted to the detection device 9 after a high-frequency component applied from the power source 8 is removed by the high frequency cut-off filter 17. Hence, the detection device 9 can detect a change in the impedance after high-frequency noise applied from the power source 8 is removed. Thus, the detection device 9 can detect a vital parameter with high accuracy.

The detection device 9 is capable of acquiring a predetermined vital parameter (in the present embodiment, an electrocardiogram) by detecting the change in the impedance in the body of the patient in accordance with the electrical signal detected by the body-surface electrode D3. That is, in the present embodiment, the electrical signal from the body of the patient can be detected by the pair of the venous electrode D2 and the body-surface electrode D3, and the detection device 9 can acquire in real time an electrocardiogram as a vital parameter in accordance with the detected electrical signal. Thus, in the present embodiment, the venous electrode D2 also serves as a counter electrode for the detection device 9 to detect the change in the impedance.

The monitoring device 10 is electrically connected to the venous electrode D2 and to the detection device 9 and is capable of monitoring in real time the current flowing through the venous electrode D2, and the change in the impedance in the body of the patient that is detected by the detection device 9. The monitoring device 10, which is connected to the venous electrode D2 in the present embodiment, may alternatively be electrically connected to the arterial electrode D1 so as to monitor in real time the current flowing through the arterial electrode D1 and the change in the impedance in the body of the patient that is detected by the detection device 9.

The identifying device 11 is electrically connected to the detection device 9 and to the monitoring device 10 and is capable of identifying a dislodged state where the arterial puncture needle (a) or the venous puncture needle (b) is dislodged from the patient, in accordance with the current value and the change in the impedance that are the objects of monitoring by the monitoring device 10. Specifically, if a dislodged state where the arterial puncture needle (a) or the venous puncture needle (b) is dislodged from the patient occurs, the current from the power source 8 does not reach the venous electrode D2. Consequently, the current value to be monitored by the monitoring device 10 becomes undetectable, and the value (a waveform) detected by the detection device 9 intermits as illustrated in FIG. 6. If such a situation occurs, the identifying device 11 can identify the situation as a dislodged state where the arterial puncture needle (a) or the venous puncture needle (b) is dislodged from the patient.

In addition to the dislodged state of the arterial puncture needle or the venous puncture needle, the identifying device 11 according to the present embodiment is capable of identifying whether the state of puncture is unstable. For example, if the state of puncture with the arterial puncture needle (a) becomes unstable (if the puncture needle is about to be dislodged from the blood vessel), as summarized in FIG. 8(a), noise increases in the electrical signal for the identification of needle dislodgement (see FIG. 5) while the heart rate (the change in the impedance) detected by the detection device 9 is normal. If the arterial puncture needle (a) is dislodged, as summarized in the same drawing, the dislodgement is identified while the heart rate (the change in the impedance) detected by the detection device 9 is normal.

On the other hand, if the state of puncture with the venous puncture needle (b) becomes unstable (if the puncture needle is about to be dislodged from the blood vessel), as summarized in FIG. 8(b), noise increases in the electrical signal for the identification of needle dislodgement (see FIG. 5) while noise also increases in the heart rate (the change in the impedance) detected by the detection device 9. If the venous puncture needle (b) is dislodged, as summarized in the same drawing, the dislodgement is identified while the heart rate (the change in the impedance) detected by the detection device 9 becomes undetectable (see FIG. 6).

When the identifying device 11 according to the present embodiment identifies any dislodged state, the identifying device 11 can identify which of the arterial puncture needle (a) and the venous puncture needle (b) is dislodged. That is, as summarized in FIG. 8(a), if the arterial puncture needle (a) is dislodged, the dislodgement is identified while the heart rate (the change in the impedance) is detected normally. On the other hand, if the venous puncture needle (b) is dislodged, as summarized in FIG. 8(b), the dislodgement is identified while the heart rate (the change in the impedance) becomes undetectable. With the detection of the above difference, when any dislodged state is identified, which of the arterial puncture needle (a) and the venous puncture needle (b) is dislodged can be identified.

In the present embodiment, for each of the body-surface electrode D3, the arterial electrode D1, and the venous electrode D2, a state of being in unstable contact and a state of being detached are identifiable. For example, if the body-surface electrode D3 is in unstable contact (a state where the body-surface electrode D3 is in contact but is very likely to be detached), as summarized in FIG. 7(a), the identification of needle dislodgement is performed normally while noise increases in the heart rate (the change in the impedance) detected by the detection device 9. If the body-surface electrode D3 is detached, as summarized in the same drawing, the identification of needle dislodgement is performed normally while the heart rate (the change in the impedance) detected by the detection device 9 becomes undetectable. In such a state of detection, the identifying device 11 can identify the body-surface electrode D3 to be in unstable contact or to be detached.

If the arterial electrode D1 is in unstable contact (a state where the arterial electrode D1 is in contact but is very likely to be detached), as summarized in FIG. 7(b), noise increases in the identification of needle dislodgement while the heart rate (the change in the impedance) detected by the detection device 9 is normal. If the arterial electrode D1 is detached, as summarized in the same drawing, the identification of needle dislodgement is performed (this case results in misidentification) while the heart rate (the change in the impedance) detected by the detection device 9 is normal. In such a state of detection, the identifying device 11 can identify the arterial electrode D1 to be in unstable contact or to be detached.

If the venous electrode D2 is in unstable contact (a state where the venous electrode D2 is in contact but is very likely to be detached), as summarized in FIG. 7(c), noise increases in the identification of needle dislodgement while noise also increases in the heart rate (the change in the impedance) detected by the detection device 9. If the venous electrode D2 is detached, as summarized in the same drawing, the identification of needle dislodgement is performed (this case results in misidentification) while the heart rate (the change in the impedance) detected by the detection device 9 becomes undetectable. In such a state of detection, the identifying device 11 can identify the venous electrode D2 to be in unstable contact or to be detached.

In addition to the above, the identifying device 11 may be configured to identify the dislodgement of the arterial puncture needle (a) with the detection of bubbles by the bubble detection device 5. Specifically, if the arterial puncture needle (a) is dislodged from the patient and falls into a dislodged state while the blood is extracorporeally circulating through the blood circuit 1 with the activation of the peristaltic blood pump 3, air is taken in from the arterial puncture needle (a). Therefore, if such air is detected by the bubble detection device 5, the dislodged state of the arterial puncture needle (a) can be identified.

The informing device 12 is electrically connected to the identifying device 11. If the identifying device 11 identifies the arterial puncture needle (a) or the venous puncture needle (b) to be in the dislodged state, the informing device 12 provides information on the dislodged state. The informing device 12 informs medical staff nearby of the identification (detection) of the dislodged state of the arterial puncture needle (a) or the venous puncture needle (b) by providing a predetermined notification (for example, an indication on a display such as a monitor, generation of a voice or a sound effect, lighting or blinking of a warning lamp, or the like).

According to the above embodiment, the power source 8 is capable of causing a current to flow through the arterial puncture needle (a) and the venous puncture needle (b) that are stuck in the patient, by applying a voltage between the arterial electrode D1 and the venous electrode D2. Therefore, even if the body-surface electrode D3 is detached from the patient, the identification of a dislodged state of the arterial puncture needle (a) or the venous puncture needle (b) can be performed continuously. In particular, when the identifying device 11 according to the present embodiment identifies any dislodged state, the identifying device 11 can identify which of the arterial puncture needle (a) and the venous puncture needle (b) is dislodged. Therefore, a countermeasure for the dislodgement can be taken accurately and smoothly.

Furthermore, the arterial electrode D1 or the venous electrode D2 also serves as a counter electrode for the detection device 9 to detect the change in the impedance. Therefore, the number of electrodes to be attached in the blood purification treatment can be reduced, and the ease of work can be increased. If the bubble detection device 5 capable of detecting the flow of bubbles is attached to the distal end part of the arterial blood circuit 1a and the identifying device 11 is configured to identify the dislodgement of the arterial puncture needle (a) with the detection of bubbles by the bubble detection device 5, when any dislodged state is identified, the dislodged state can be distinguished more accurately between the dislodged state of the arterial puncture needle (a) and the dislodged state of the venous puncture needle (b).

In addition to the dislodged state of the arterial puncture needle (a) or the venous puncture needle (b), the identifying device 11 according to the embodiment is capable of identifying whether the state of puncture is unstable or whether the electrode (the arterial electrode D1, the venous electrode D2, or the body-surface electrode D3) is unstably in contact or is detached. Therefore, a countermeasure can be taken before any dislodged state occurs or before the arterial electrode D1, the venous electrode D2, or the body-surface electrode D3 is detached. Furthermore, if the identifying device 11 identifies the arterial puncture needle (a) or the venous puncture needle (b) to be in the dislodged state, the informing device 12 provides information on the dislodged state. Therefore, medical staff or the like nearby can immediately notice the dislodged state and can immediately take a countermeasure.

While the present embodiment has been described above, the present invention is not limited thereto. The heart rate (the electrocardiogram) detected by the detection device 9 may be another predetermined vital parameter. For example, the detection device 9 may be a body composition monitor or an electromyogram that is capable of measuring the amount of body fluid, the amount of muscle, or the like of the patient in accordance with the change in the impedance detected by the body-surface electrode D3. If a body composition monitor is employed, the body-surface electrode is preferably attached to a position near an ankle of the patient. If the amount of body water is measured with a body composition monitor, a suitable dialysis treatment can be given. If an electromyogram is employed, abnormal trembling or the like of the patient can be detected, leading to an improvement in safety.

Furthermore, while the detection device 9, the monitoring device 10, and the identifying device 11 are provided in the apparatus body B in the present embodiment, the three may be provided in another apparatus (including a personal computer or the like) that is separate from the apparatus body B. Moreover, the applicable blood purification apparatus is not limited to a hemodialysis apparatus and may be any apparatus for giving another kind of blood purification treatment.

The present invention is applicable to any blood purification apparatus, including those having different external shapes, other additional functions, and so forth, as long as the blood purification apparatus includes a detection device capable of acquiring a predetermined vital parameter by detecting a change in the impedance in the body of the patient in accordance with an electrical signal detected by a body-surface electrode; a monitoring device capable of monitoring in real time a current flowing through an arterial electrode or a venous electrode, and the change in the impedance in the body of the patient that is detected by the detection device; and an identifying device capable of identifying a dislodged state where an arterial puncture needle or a venous puncture needle is dislodged from the patient, in accordance with the current value and the change in the impedance that are objects of monitoring by the monitoring device.

REFERENCE SIGN LIST 1 blood circuit
1a arterial blood circuit
1b venous blood circuit
2 dialyzer (blood purification device)
3 peristaltic blood pump
4 air-trap chamber
5 bubble detection device
6 ultrafiltration pump
7 duplex pump
8 power source
9 detection device
10 monitoring device
11 identifying device
12 informing device
13 differential amplifier
14 rectifier circuit
15 impedance-adjusting device
16 differential amplifier
17 high frequency cut-off filter
D1 arterial electrode
D2 venous electrode
D3 body-surface electrode
a arterial puncture needle
b venous puncture needle
B apparatus body
L1 dialysate introduction line
L2 dialysate drain line
R lock ring

The invention claimed is:

1. A blood purification apparatus comprising:
an arterial blood circuit provided with an arterial puncture needle at a distal end, the arterial puncture needle being stickable into a patient;
a venous blood circuit provided with a venous puncture needle at a distal end, the venous puncture needle being stickable into the patient; and
a blood purification device connected to a proximal end of the arterial blood circuit and to a proximal end of the venous blood circuit, the device purifying blood of the patient that extracorporeally circulates through the arterial blood circuit and the venous blood circuit,
wherein the blood purification apparatus includes
an arterial electrode through which a voltage is applied to the blood flowing in the arterial blood circuit;
a venous electrode through which the voltage is applied to the blood flowing in the venous blood circuit;
a power source that causes a current to flow in the blood through the arterial puncture needle and the venous puncture needle that are stuck in the patient, by applying the voltage between the arterial electrode and the venous electrode;
a body-surface electrode closely attached to a body surface of the patient and that detects an electrical signal from a body of the patient;
a detection device that acquires a predetermined vital parameter by detecting a change in an impedance in the body of the patient in accordance with the electrical signal detected by the body-surface electrode;
a monitoring device that monitors in real time the current flowing through the arterial electrode or the venous electrode, and the change in the impedance in the body of the patient that is detected by the detection device; and
an identifying device that identifies a dislodged state where the arterial puncture needle or the venous puncture needle is dislodged from the patient, in accordance with the change in the impedance; and
wherein when the identifying device identifies any dislodged state, the identifying device identifies which of the arterial puncture needle and the venous puncture needle is dislodged; and
wherein the arterial electrode or the venous electrode also serves as a counter electrode for the detection device to detect the change in the impedance.

2. The blood purification apparatus according to claim 1, wherein the arterial blood circuit is provided with a bubble detection device at a distal end part, the bubble detection device detecting a flow of bubbles, and wherein the identifying device identifies the dislodgement of the arterial puncture needle with the detection of bubbles by the bubble detection device.

3. The blood purification apparatus according to claim 1, wherein the identifying device that identifies the dislodged state of the arterial puncture needle or the venous puncture needle further identifies whether a state of puncture is unstable or whether any of the electrodes is in unstable contact or is detached.

4. The blood purification apparatus according to claim 1, further comprising an informing device that provides information on the dislodged state if the identifying device identifies the arterial puncture needle or the venous puncture needle to be in the dislodged state.

5. The blood purification apparatus according to claim 2, wherein the arterial electrode or the venous electrode also serves as a counter electrode for the detection device to detect the change in the impedance.

6. The blood purification apparatus according to claim 3, wherein the arterial blood circuit is provided with a bubble detection device at a distal end part, the bubble detection device detecting a flow of bubbles, and wherein the identifying device identifies the dislodgement of the arterial puncture needle with the detection of bubbles by the bubble detection device.

7. The blood purification apparatus according to claim 4, wherein the arterial blood circuit is provided with a bubble detection device at a distal end part, the bubble detection device detecting a flow of bubbles, and wherein the identifying device identifies the dislodgement of the arterial puncture needle with the detection of bubbles by the bubble detection device.

8. The blood purification apparatus according to claim 7, wherein the identifying device that identifies the dislodged state of the arterial puncture needle or the venous puncture needle further identifies whether a state of puncture is unstable or whether any of the electrodes is in unstable contact or is detached.

9. The blood purification apparatus according to claim 8, further comprising an informing device that provides information on the dislodged state if the identifying device identifies the arterial puncture needle or the venous puncture needle to be in the dislodged state.

* * * * *